United States Patent [19]
Baracchini, Jr. et al.

[11] Patent Number: 5,807,838
[45] Date of Patent: Sep. 15, 1998

[54] OLIGONUCLEOTIDE MODULATION OF MULTIDRUG RESISTANCE-ASSOCIATED PROTEIN

[75] Inventors: Edgardo Baracchini, Jr., San Diego; Clarence Frank Bennett, Carlsbad, both of Calif.

[73] Assignee: Isis Pharmaceuticals, Inc., Carlsbad, Calif.

[21] Appl. No.: 628,731

[22] PCT Filed: Sep. 23, 1994

[86] PCT No.: PCT/US94/10827

§ 371 Date: Apr. 16, 1996

§ 102(e) Date: Apr. 16, 1996

[87] PCT Pub. No.: WO95/10938

PCT Pub. Date: Apr. 27, 1995

[51] Int. Cl.[6] .............................. A61K 48/00; C07H 21/04
[52] U.S. Cl. .............................. 514/44; 536/24.5; 935/8; 935/34
[58] Field of Search .............................. 514/44; 536/24.5, 536/23.5, 24.31; 435/6; 935/34, 8

[56] References Cited

U.S. PATENT DOCUMENTS

| | | | |
|---|---|---|---|
| 4,806,463 | 2/1989 | Goodchild et al. | 435/5 |
| 4,999,421 | 3/1991 | Brunck et al. | 530/350 |
| 5,004,810 | 4/1991 | Draper | 536/27 |
| 5,087,617 | 2/1992 | Smith | 514/44 |
| 5,098,890 | 3/1992 | Gewirtz et al. | 514/44 |
| 5,135,917 | 8/1992 | Burch | 514/44 |
| 5,166,195 | 11/1992 | Ecker | 514/44 |
| 5,194,428 | 3/1993 | Agrawal et al. | 514/44 |
| 5,242,906 | 9/1993 | Pagano et al. | 514/44 |
| 5,264,423 | 11/1993 | Cohen et al. | 514/44 |
| 5,276,019 | 1/1994 | Cohen et al. | 514/44 |
| 5,286,717 | 2/1994 | Cohen et al. | 514/44 |

OTHER PUBLICATIONS

Cole et al., "Overexpression of a Transporter Gene in a Multidrug–Resistant Human Lung Cancer Cell", *Science* 1992, 258, 1650–54.

Cole et al., "Multidrug Resistance–Associated Protein: Sequence Correction", *Science* 1993, 260, 879.

Mirski et al., "Multidrug Resistance in a Human Small Cell Lung Cencer Cell Line Selected in Adriamycin," *Cancer Res.* 1987, 47, 2594–98.

Mirski et al., "Antigens Associated with Multidrug Resistance in H69AR a Small Cell Lung Cancer Cell Line", *Cancer Res* 1989, 49, 5719–24.

Nielsen et al., "Sequence–Selective Recognition of DNA by Strand Displacement with a Thymine–Substituted Polymide," *Science* 1991, 254, 1497.

Sambrook et al., "*Molecular Cloning. A Laboratory Manual*," Cold Spring Harbor Laboratory Press, 1989, vol. 2, pp. 11.31–11.32.

Sambrook et al., *Molecular Cloning. A Laboratory Manual*, Cold Spring Harbor Laboratory Press, 1989, vol. 2, p. 10.59.

Slovak et al., "Localization of a Novel Multidrug Resistance–Associated Gene in the HT1080/DR4 and H69AR Human Tumor Cell Lines," *Cancer Res.* 1993, 53, 3221–3225.

Thierry et al., "Overcoming Multidrug Resistance in Human Tumor Cells Using Free and Liposomally Encapsulated Antisense Oligodeoxyucleotides," *Biochem. Biophys. Res. Comm.* 1993, 190, 952–960.

Vasanthakumar et al., "Modulation of Drug Resistance in a Daunorubicin Resistnat Subline with Oligonucleoside Methylphosphonates," *Cancer Commun.* 1989, 1, 225–232.

*Primary Examiner*—Bruce R. Campell
*Attorney, Agent, or Firm*—Law Offices of Jane Massey Licata

[57] ABSTRACT

Compositions and methods are provided for the treatment and diagnosis of diseases or conditions amenable to treatment through modulation of the synthesis or metabolism of multidrug resistance-associated protein (MRP). In accordance with preferred embodiments, oligonucleotides are provided which are specifically hybridizable with nucleic acids encoding multidrug resistance-associated protein (MRP). Methods of treating animals suffering from diseases or conditions amenable to therapeutic intervention by modulating multidrug resistance with an oligonucleotide specifically hybridizable with RNA or DNA corresponding to multidrug resistance-associated protein (MRP) are disclosed. Methods of preventing the development of multidrug resistance and of improving the efficacy of chemotherapy are also disclosed.

28 Claims, No Drawings

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 1:

C G G G G C C G C A      A C G C C G C C U G                                                     2 0

( 2 ) INFORMATION FOR SEQ ID NO:2:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 2:

C G G G G C C G C A      A C G C C G C C T G                                                     2 0

( 2 ) INFORMATION FOR SEQ ID NO:3:

( i ) SEQUENCE CHARACTERISTICS:
        ( A ) LENGTH: 20

(B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 3:

GGTGATCGGG CCCGGTTGCT                       20

(2) INFORMATION FOR SEQ ID NO: 4:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 4:

CCGGTGGCGC GGGCGGCGGC                       20

(2) INFORMATION FOR SEQ ID NO: 5:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 5:

AGCCCCGGAG CGCCATGCCG                       20

(2) INFORMATION FOR SEQ ID NO: 6:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 6:

TCGGAGCCAT CGGCGCTGCA                       20

(2) INFORMATION FOR SEQ ID NO: 7:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 7:

GGCACCCACA CGAGGACCGT                       20

(2) INFORMATION FOR SEQ ID NO: 8:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes ( x i ) SEQUENCE DESCRIPTION: SEQ ID NO: 8:

TGCTGTTCGT GCCCCCGCCG 20

( 2 ) INFORMATION FOR SEQ ID NO: 9:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 9:

CGCGCTGCTT CTGGCCCCA 20

( 2 ) INFORMATION FOR SEQ ID NO: 10:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 10:

GCGGCGATGG GCGTGGCCAG 20

( 2 ) INFORMATION FOR SEQ ID NO: 11:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 11:

CAGGAGGTCC GATGGGGCGC 20

( 2 ) INFORMATION FOR SEQ ID NO: 12:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 12:

GCTCACACCA AGCCGGCGTC 20

( 2 ) INFORMATION FOR SEQ ID NO: 13:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 13:

AGGCCCTGCA GTTCTGACCA 20

( 2 ) INFORMATION FOR SEQ ID NO: 14:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 14:

CTCCTCCCTG GGCGCTGGCA  20

( 2 ) INFORMATION FOR SEQ ID NO: 15:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 15:

ACCGGATGGC GGTGGCTGCT  20

( 2 ) INFORMATION FOR SEQ ID NO: 16:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 16:

CGCATCTCTG TCTCTCCTGG  20

( 2 ) INFORMATION FOR SEQ ID NO: 17:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 17:

CAGAAGCCCC GGAGCGCCAT  20

( 2 ) INFORMATION FOR SEQ ID NO: 18:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 18:

GCCCCCGCCG TCTTTGACAG  20

( 2 ) INFORMATION FOR SEQ ID NO: 19:

( i ) SEQUENCE CHARACTERISTICS:
        ( A ) LENGTH: 20

(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 19:

GTGATGCTGT TCGTGCCCCC 20

(2) INFORMATION FOR SEQ ID NO: 20:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 20:

CTCACGGTGA TGCTGTTCGT 20

(2) INFORMATION FOR SEQ ID NO: 21:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 21:

CCCCCAGACA GGTTCACGCC 20

(2) INFORMATION FOR SEQ ID NO: 22:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 22:

CTGGCCCCCA GACAGGTTCA 20

(2) INFORMATION FOR SEQ ID NO: 23:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 23:

GCCAGGCTCA CGCGCTGCTT 20

(2) INFORMATION FOR SEQ ID NO: 24:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes ( x i ) SEQUENCE DESCRIPTION: SEQ ID NO: 24:

CACAGCCAGT TCCAGGCAGG 20

( 2 ) INFORMATION FOR SEQ ID NO: 25:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 25:

CCTGGGTCTT CACAGCCAGT 20

OLIGONUCLEOTIDE MODULATION OF MULTIDRUG RESISTANCE-ASSOCIATED PROTEIN

FIELD OF THE INVENTION

This invention relates to diagnostics, research reagents and therapies for multidrug resistance and for disease states which respond to modulation of the phenomenon of multidrug resistance. In particular, this invention relates to antisense oligonucleotide interactions with certain messenger ribonucleic acids (mRNAs) or DNAs involved in the synthesis of the multidrug resistance-associated protein (MRP). Antisense oligonucleotides designed to hybridize to the MRNA encoding MRP are provided. These oligonucleotides have been found to lead to the modulation of the activity of the RNA or DNA, and thus to the modulation of the synthesis and metabolism of MRP. Palliation and therapeutic effect result. These oligonucleotides can also be used in assays and diagnostics, and can be useful in distinguishing MRP-associated multidrug resistance from other multidrug resistance pathways.

BACKGROUND OF THE INVENTION

Acquired resistance to chemotherapy is a major problem in treatment of cancer by conventional cytotoxic drugs. Tumors may initially respond well to chemotherapy but later become resistant to a variety of unrelated drugs, leading to relapse. Multidrug resistance can arise via one of several independent pathways, any or all of which may be amenable to inhibition. One cause of multidrug resistance is believed to be overexpression of a transmembrane transport protein known as P-glycoprotein or MDR protein. Another distinct cause of multidrug resistance is believed to be overexpression of a member of the ATP-binding cassette transmembrane transporter superfamily known as multidrug resistance-associated protein (MRP). This protein is overexpressed in certain tumor cell lines which are multidrug resistant but do not overexpress P-glycoprotein. Cole et al. *Science* 1992, 258, 1650–1654; Slovak et al. *Cancer Res.* 1993, 53, 3221–3225. The gene encoding MRP was initially isolated from a multidrug-resistant small-cell lung cancer cell line. Small-cell lung cancer accounts for 20–25% of all lung cancer. Up to 90% of small-cell lung cancers respond initially to chemotherapy, but nearly all become multidrug resistant, leading to relapse. Compositions and methods for modulating and detecting MRP are the subject of this invention.

Agents capable of reversing the phenomenon of multidrug resistance and thus "sensitizing" the drug resistant tumors to chemotherapy are desired. Cyclosporin A and other agents are able to reverse doxorubicin resistance in cells which overexpress MDR, but clinical use of these compounds is limited by their cytotoxicity. Further, these reversing agents do not work in cells which overexpress MRP. Antisense oligonucleotides targeted to the MDR mRNA encoding P-glycoprotein have been used to partially reverse the multidrug resistance phenotype. Thierry et al. *Biochem. Biophys. Res. Comm.* 1993, 190, 952–960. Others have demonstrated complete inhibition of P-glycoprotein (MDR protein) synthesis by 15-mer antisense methylphosphonate oligonucleotides. They have further shown that oligonucleotides complementary to the initiation codon and a few codons upstream of the mdr1 gene are most effective, but lead to only a partial decrease in drug resistance. Larger oligonucleotides, such as 21-mers, showed decreased solubility and permeability. Vasanthakumar, G. and N. K. Ahmed *Cancer Commun.* 1989, 1, 225–232.

While compositions and methods for reversing P-glycoprotein (MDR)-associated multidrug resistance or MDR synthesis have shown limited success, there remains a long-felt need for compositions and methods for modulation and diagnosis of other types of multidrug resistance. Oligonucleotides that are specifically hybridizable with MRP mRNA are desired for their diagnostic and therapeutic utility. Interference with MRP expression is desired as a means of reversing the multidrug resistance phenomenon, and making a distinction between multidrug resistance due to MRP and that due to other causes. Interference with MRP expression is also desired for improving the efficacy of conventional methods of cancer chemotherapy, particularly of lung cancer, most particularly of small-cell lung cancer.

SUMMARY OF THE INVENTION

In accordance with the present invention, oligonucleotides are provided which specifically hybridize with nucleic acids encoding multidrug resistance-associated protein (MRP). The oligonucleotides are designed to bind either directly to mRNA or to a selected DNA portion forming a triple stranded structure, thereby modulating the amount of MRNA made from the gene. In either case, expression of MRP protein is ultimately modulated. "Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which are known to form two hydrogen bonds between them. "Specifically hybridizable" indicates a sufficient degree of complementarity to avoid non-specific binding of the oligonucleotide to non-target sequences. It is understood that an oligonucleotide need not be 100% complementary to its target nucleic acid sequence to be specifically hybridizable.

The relationship between an oligonucleotide and its complementary target nucleic acid is commonly denoted as "antisense." In the context of the present invention, the "target" is a nucleic acid encoding multi-drug resistance-associated protein (MRP); in other words, the MRP gene or mRNA expressed from the MRP gene.

It is preferred to target specific genes for antisense attack. It has been discovered that the gene coding for MRP is particularly useful for this approach. Inhibition of MRP expression is expected to be useful for the treatment of multidrug resistance. However, "modulation" in the context of this invention means either an increase or decrease (stimulation or inhibition) of MRP expression.

Methods of modulating the synthesis of MRP in cells and tissues comprising contacting an animal suspected of having multidrug-resistant cells or tissues with an oligonucleotide specifically hybridizable with nucleic acids encoding the MRP protein are provided.

Methods of treating an animal suspected of having a condition characterized by elevated levels of MRP are also provided. Such methods comprise administering to an animal a therapeutically effective amount of an oligonucleotide specifically hybridizable with nucleic acids encoding the MRP protein.

Other aspects of the invention are directed to methods for improving the efficacy of chemotherapy and preventing the development of multidrug resistance during chemotherapeutic drug treatment of a disease. Such methods comprise administering to an animal an appropriate amount of oligonucleotide specifically hybridizable with nucleic acids encoding the MRP protein in conjunction with a chemotherapeutic drug treatment.

Methods for diagnosis are also a part of this invention, and include methods for determining MRP-associated multidrug resistance as being distinct from other pathways of multidrug resistance development. Such methods comprise contacting cells or tissues or bodily fluids from the diseased animals with oligonucleotides in accordance with this invention in order to detect MRP overexpression.

DETAILED DESCRIPTION OF PREFERRED EMBODIMENTS

Oligonucleotides have recently become accepted as therapeutic moieties in the treatment of disease states in animals and man. For example, workers in the field have now identified antisense, triplex and other oligonucleotide therapeutic compositions which are capable of modulating expression of genes implicated in viral, fungal and metabolic diseases.

U.S. Pat. No. 5,098,890 is directed to antisense oligonucleotide therapies for certain cancerous conditions. U.S. Pat. No. 5,135,917 provides antisense oligonucleotides that inhibit human interleukin-1 receptor expression. U.S. Pat. No. 5,087,617 provides methods for treating cancer patients with antisense oligonucleotides. U.S. Pat. No. 5,166,195 provides oligonucleotide inhibitors of HIV. U.S. Pat. No. 5,004,810 provides oligomers capable of hybridizing to herpes simplex virus Vmw65 MRNA and inhibiting replication. U.S. Pat. No. 5,194,428 provides antisense oligonucleotides having antiviral activity against influenza virus. U.S. Pat. No. 4,806,463 provides antisense oligonucleotides and methods using them to inhibit HTLV-III replication. U.S. Pat. No. 5,286,717 provides oligonucleotides having a complementary base sequence with a portion of an oncogene. U.S. Pat. Nos. 5,276,019 and 5,264,423 are directed to oligonucleotide analogs used to prevent replication of foreign nucleic acids in cells. U.S. Pat. No. 4,689,320 is directed to antisense oligonucleotides as antiviral agents specific to CMV. U.S. Pat. No. 5,098,890 provides oligonucleotides complementary to at least a portion of the mRNA transcript of the human c-myb gene. U.S. Pat. No. 4,999,421 is directed to peptides expressed by the antisense strand of HTLV-1. U.S. Pat. No. 5,242,906 provides antisense oligonucleotides useful in the treatment of latent EBV infections. Antisense oligonucleotides have been safely administered to humans and several clinical trials are presently underway. It is, thus, established that oligonucleotides can be useful therapeutic instrumentalities and that the same can be configured to be useful in treatment regimes for treatment of cells and animals, especially humans.

For therapeutics, an animal suspected of having a disease which can be treated by decreasing the expression of MRP is treated by administering oligonucleotides in accordance with this invention. Oligonucleotides may be formulated in a pharmaceutical composition, which may include carriers, thickeners, diluents, buffers, preservatives, surface active agents, liposomes or lipid formulations and the like in addition to the oligonucleotide. Pharmaceutical compositions may also include one or more active ingredients such as antimicrobial agents, antiinflammatory agents, anesthetics, and the like in addition to oligonucleotide. Oligonucleotides may be administered in conjunction with conventional cancer chemotherapeutic drugs which are well known to those skilled in the art.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms or gloves may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, liposomes, diluents and other suitable additives.

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual oligonucleotides, and can generally be estimated based on $EC_{50}$'s in in vitro and in vivo animal studies. In general, dosage is from 0.01 $\mu$g to 100 g and may be administered once daily, weekly, monthly or yearly, or even every 2 to 20 years.

The present invention employs oligonucleotides for use in antisense inhibition of the function of RNA and DNA encoding multidrug resistance-associated protein (MRP). In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures. Summerton, J. E. and Weller, D. D., U.S. Pat. No. 5,034,506. In other preferred embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt Science 1991, 254, 1497. Other preferred oligonucleotides may contain sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; CF$_3$; OCF$_3$; O-, S-, or N-alkyl; O-, S-, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Base modifications or "universal" bases such as inosine may also be included.

The oligonucleotides in accordance with this invention preferably comprise from about 8 to about 30 nucleotides. It is more preferred that such oligonucleotides comprise from about 15 to 25 nucleotides. As will be appreciated, a nucleotide is a base-sugar combination suitably bound to an adjacent nucleotide through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; however, the actual synthesis of the oligonucleotides is well within the talents of the routineer. It is also known to use similar techniques to prepare other oligonucleotides such as the phosphorothioates and alkylated derivatives.

In accordance with this invention, persons of ordinary skill in the art will understand that messenger RNA identified by the open reading frames (ORFs) of the DNA from which they are transcribed includes not only the information from the ORFs of the DNA, but also associated ribonucleotides which form regions known to such persons as the 5'-untranslated region, the 3'-untranslated region, intervening sequence (intron) ribonucleotides and intron/exon junctions. Thus, oligonucleotides may be formulated in accordance with this invention which are targeted wholly or in part to these associated ribonucleotides as well as to the informational ribonucleotides. In preferred embodiments, the oligonucleotide is specifically hybridizable with a transcription initiation site, a translation initiation site, coding sequences and sequences in the 5'- and 3'-untranslated regions.

In accordance with this invention, the oligonucleotide is specifically hybridizable with portions of nucleic acids encoding multidrug resistance-associated protein (MRP). MRP belongs to the superfamily of ATP-binding cassette transport systems. This family includes the cystic fibrosis transmembrane conductance regulator, P-glycoprotein, and other transport proteins. The human MRP protein is 1531 amino acids in length and is encoded by an mRNA which is approximately 6.5 kb in length. Cole et al. *Science* 1992, 258, 1650–1654; Cole et al. *Science* 1993, 260, 879 (sequence correction); Slovak et al. *Cancer Res.* 1993, 53, 3221–3225. Antisense oligonucleotides (shown in Table 1) were designed to be specifically hybridizable with sequences in the 5'-untranslated region, 3'-untranslated region and coding region of the MRP gene. The sequence of the MRP gene is available in publications [Cole et al. *Science* 1992, 258, 1650–1654; Cole et al. *Science* 1993, 260, 879 (sequence correction)] or through Genbank accession number L05628.

TABLE 1

Antisense Oligonucleotides Specifically Hybridizable With MRP
(All are phosphorothioates; ISIS 7607 is also 2'-O-methyl)

| ISIS # | TARGET REGION | SEQUENCE | SEQ ID NO: |
|---|---|---|---|
| 7607 | 5' UTR | CGG GGC CGC AAC GCC GCC UG | 1 |
| 7608 | 5' UTR | CGG GGC CGC AAC GCC GCC TG | 2 |
| 7606 | 5' UTR | GGT GAT CGG GCC CGG TTG CT | 3 |
| 7595 | 5' UTR | CCG GTG GCG CGG GCG GCG GC | 4 |
| 7592 | AUG | AGC CCC GGA GCG CCA TGC CG | 5 |
| 7593 | Coding | TCG GAG CCA TCG GCG CTG CA | 6 |
| 7594 | Coding | GGC ACC CAC ACG AGG ACC GT | 7 |
| 7597 | Coding | TGC TGT TCG TGC CCC CGC CG | 8 |
| 7598 | Coding | CGC GCT GCT TCT GGC CCC CA | 9 |
| 7599 | Coding | GCG GCG ATG GGC GTG GCC AG | 10 |
| 7600 | Coding | CAG GAG GTC CGA TGG GGC GC | 11 |
| 7601 | Coding | GCT CAC ACC AAG CCG GCG TC | 12 |
| 7603 | 3' UTR | AGG CCC TGC AGT TCT GAC CA | 13 |
| 7605 | 3' UTR | CTC CTC CCT GGG CGC TGG CA | 14 |
| 7602 | 3' UTR | ACC GGA TGG CGG TGG CTG CT | 15 |
| 7604 | 3' UTR | CGC ATC TCT GTC TCT CCT GG | 16 |

Preferred oligonucleotides useful in the invention comprise one of these sequences, or part thereof.

H69AR cells were treated with phosphorothioate oligonucleotides (SEQ ID NO: 1–16) in the presence of LIPOFECTIN (GIBCO/BRL) as described in the following examples. Oligonucleotides ISIS 7597 and ISIS 7598 (SEQ ID NO: 8 and SEQ ID NO: 9), both specifically hybridizable to the coding region of MRP, consistently inhibited steady-state MRP protein levels by greater than 30% compared to LIPOFECTIN controls in multiple ELISA experiments. In one experiment, ISIS 7597 inhibited MRP protein levels by over 95%. Oligonucleotides ISIS 7597 and 7598 are therefore preferred. It should be noted that the ELISA assay measures steady-state levels of MRP protein; because of the long half-life of the MRP protein, complete inhibition of MRP protein synthesis would be expected to be reflected as a decrease, but not complete loss, of MRP protein in these assays. This level of inhibition in this assay is considered to be significant. In Northern blot analysis of the effects of ISIS 7597 and 7598 on MRP mRNA levels, both oligonucleotides were demonstrated to virtually eliminate MRP mRNA expression.

Based on results obtained with the oligonucleotides of Table 1, additional phosphorothioate oligonucleotides were designed. These oligonucleotides are shown in Table 2.

TABLE 2

Phosphorothioate Antisense Oligonucleotides
Specifically Hybridizable With MRP

| ISIS # | TARGET REGION | SEQUENCE | SEQ ID NO: |
|---|---|---|---|
| 8356 | AUG    | CAG AAG CCC CGG AGC GCC AT | 17 |
| 8358 | Coding | GCC CCC GCC GTC TTT GAC AG | 18 |
| 8359 | Coding | GTG ATG CTG TTC GTG CCC CC | 19 |
| 8357 | Coding | CTC ACG GTG ATG CTG TTC GT | 20 |
| 8362 | Coding | CCC CCA GAC AGG TTC ACG CC | 21 |
| 8361 | Coding | CTG GCC CCC AGA CAG GTT CA | 22 |
| 8360 | Coding | GCC AGG CTC ACG CGC TGC TT | 23 |
| 8363 | 3' UTR | CAC AGC CAG TTC CAG GCA GG | 24 |
| 8364 | 3' UTR | CCT GGG TCT TCA CAG CCA GT | 25 |

Chimeric oligonucleotides having SEQ ID NO: 8 were prepared. These oligonucleotides had uniform phosphorothioate backbones and central "gap" regions of 8 deoxynucleotides flanked by 2 regions of 2'-O-propyl modified nucleotides (ISIS 9659) or 2'-fluoro modified nucleotides (ISIS 9661).

Further, chimeric oligonucleotides having SEQ ID NO: 9 were prepared. These oligonucleotides had uniform phosphorothioate backbones and central "gap" regions of 8 deoxynucleotides flanked by 2 regions of 2'-O-propyl modified nucleotides (ISIS 9660) or 2'-fluoro modified nucleotides (ISIS 9662).

The present invention is also suitable for detection of MRP overexpression in tissue or other samples from patients who have developed multidrug resistance. A number of assays may be formulated employing the present invention, which assays will commonly comprise contacting a tissue sample with an oligonucleotide of the invention under conditions selected to permit detection, and usually quantitation, of such inhibition. For example, radiolabelled oligonucleotides can be prepared by $^{32}P$ labeling at the 5' end with polynucleotide kinase. Sambrook et al., *Molecular Cloning. A Laboratory Manual,* Cold Spring Harbor Laboratory Press, 1989, Volume 2, pg. 10.59. Radiolabeled oligonucleotides are then contacted with tissue or cell samples suspected of MRP overexpression or with RNA extracted from such samples. The sample is then washed to remove unbound oligonucleotide. Radioactivity remaining in the sample indicates bound oligonucleotide (which in turn indicates expression of the nucleic acids encoding MRP) and can be quantitated using a scintillation counter or other routine means. Comparison to appropriate controls allows overexpression of MRP to be determined. Radiolabeled oligonucleotide can also be used to perform autoradiography of tissues to determine the localization, distribution and quantitation of MRP overexpression for research, diagnostic and therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing MRP. Quantitation of the silver grains permits MRP overexpression to be detected.

Analogous assays for fluorescent detection of MRP expression can be developed using oligonucleotides of the invention which are conjugated with fluorescein or other fluorescent tag instead of radiolabeling. Such conjugations are routinely accomplished during solid phase synthesis using fluorescently-labeled amidites or CPG (e.g., fluorescein-labeled amidites or CPG available from Glen Research, Sterling, Va. See 1993 Catalog of Products for DNA Research, Glen Research, Sterling, Va, pg.21).

Each of these assay formats is known in the art. One of skill could easily adapt these known assays for detection of MRP expression in accordance with the teachings of the invention providing a novel and useful means to detect MRP expression.

In addition, the ability of the oligonucleotides of the present invention to inhibit MRP synthesis in cultured disease cells is extremely useful in distinguishing drug resistance which is MRP-associated from that which arises via another pathway. In case of a disease state such as cancer, oligonucleotide-treated cells from the drug resistant tumor sites can be cultured and screened for reversal of drug resistance, i.e., increased sensitivity to chemotherapeutic drugs as quantitated by a decrease in the $IC_{50}$ values. Those of skill in the art could then use this information to treat the disease state more efficaciously. The utility and relevance of the information provided by the use of these oligonucleotides in differentiating between types of multidrug resistance will be clear to those of skill in the art.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

Several preferred embodiments of this invention are exemplified in accordance with the following nonlimiting examples.

EXAMPLES

Example 1

Synthesis and Characterization of Oligonucleotides

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'-O-methyl phosphorothioate oligonucleotides were synthesized using 2'-O-methyl β-cyanoethyldiisopropyl-phosphoramidites (Chemgenes, Needham, Mass.) and the standard cycle for unmodified oligonucleotides, except the wait step after pulse delivery of tetrazole and base was increased to 360 seconds. The 3'-base used to start the synthesis was a 2'-deoxyribonucleotide. 2'-O-propyl oligonucleotides were prepared by a slight modification of this procedure.

2'-Fluoro phosphorothioate oligonucleotides were synthesized using 5'-dimethoxytrityl-3'-phosphoramidites and prepared as disclosed in U.S. patent application Ser. No. 463,358, filed Jan. 11, 1990, abandoned, and 566,977, filed Aug. 13, 1990, abandoned, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

After cleavage from the controlled pore glass column (Applied Biosystems) and deblocking in concentrated ammonium hydroxide at 55° C. for 18 hours, the oligonucleotides were purified by precipitation twice out of 0.5M NaCl with 2.5 volumes ethanol. Analytical gel electrophoresis was accomplished in 20% acrylamide, 8M urea, 45 mM Trisborate buffer, pH 7.0. Oligodeoxynucleotides and phosphorothioate oligonucleotides were judged from electrophoresis to be greater than 80% full length material.

The relative amounts of phosphorothioate and phosphodiester linkages obtained by this synthesis were periodically checked by $^{31}P$ NMR spectroscopy. The spectra were obtained at ambient temperature using deuterium oxide or dimethyl sulfoxide-$d_6$ as solvent. Phosphorothioate samples typically contained less than one percent of phosphodiester linkages.

Example 2

Selection and Maintenance of Multidrug Resistant Cell Line H69AR Cells

H69AR, a doxorubicin-resistant human small cell lung carcinoma cell line, was selected and maintained as described in Mirski et al. *Cancer Res.* 1987, 47, 2594–2598.

Example 3

Lipofection and Oligonucleotide Treatment of H69AR Cells for Analysis by Whole Cell ELISA $1.5 \times 10^6$ cells were plated into 35 mm tissue culture wells and allowed to attach overnight. The cells were then washed twice with 3 ml of serum-free medium prior to lipofection. Oligonucleotides were added to a concentration of 0.3 $\mu$M in 1 ml of serum-free medium in a polystyrene tube. 10 $\mu$l of LIPOFECTIN (GIBCO-BRL) was then added and the mixture was vortexed. After ten minutes at room temperature, the DNA/LIPOFECTIN suspension was added to the cells and incubated for four hours at 37° C. After this incubation, 1 ml of 20% Hyclone serum in RPMI was added and left at 37° C. overnight. The next day the suspension was removed and replaced with fresh medium. On the following day, the lipofection was repeated as before and the cells were harvested 48 hours after the second lipofection.

Example 4

Whole Cell ELISA of H69AR Cells After Oligonucleotide Treatment

Cells were harvested, counted and washed twice with PBS. Cells were resuspended at $0.5-1 \times 10^5$ cells/ml in PBS and 100 $\mu$l was plated in each well of an ELISA plate. Plates were dried overnight at 37° and autocrosslinked twice in a Stratalinker (Stratagene, La Jolla, Calif.). Plates were rehydrated in TBST, 200 $\mu$l/well for 2×5 minutes. Wells were blocked for 1.5–2 hours at room temperature with 200 $\mu$l TBST containing 5% NGS, 1% BSA. Primary antibody [50 $\mu$l of monoclonal antibody 3.186; Mirski et al. *Cancer Res.* 1989, 49, 5719–5724] diluted in blocking solution was added and plates were incubated for 1.5–2 hours in a humidified chamber at room temperature. Plates were washed 3×5 minutes with 200 $\mu$l TBST. Plates were incubated with 50 $\mu$l secondary antibody diluted in blocking solution for 1–1.5 hours at room temperature in a humidified chamber. Plates were washed for with 200 $\mu$l TBST, 3×5 minutes. Color detection was by horseradish peroxidase [incubated with 100 $\mu$l OPD/$H_2O_2$/citrate buffer (250 $\mu$l 10 mg/ml OPD in methanol/25 $\mu$l 3% $H_2O_2$/24.8 ml 0.05M citrate pH 5)] in the dark for 30 minutes at room temperature, stop reaction with 25 $\mu$l 8 N $H_2SO_4$, and read absorbance at 490 nm] or by alkaline phosphatase [incubate with 50 $\mu$l substrate solution (1 PNPP tablet in 5 ml 50 mM NaHCO$_3$, pH 9.6, 1 mM MgCl$_2$) for 30 minutes in humid chamber at room temperature, stop reaction with 50 $\mu$l 0.4M NaOH, read absorbance at 405 nm].

Example 5

RNA Analysis of H69AR Cells Treated with Antisense Oligonucleotides Specifically Hybridizable with MRP $10 \times 10^6$ cells were plated per T75 flask and allowed to attach overnight. Cells were washed twice with serum-free medium before incubation with 6 ml of oligonucleotide/LIPOFECTIN suspension (0.3 $\mu$M oligonucleotide; 10 $\mu$l LIPOFECTIN per ml of serum-free medium) at 37° C. for 4 hours after which 6 ml of 20% Hyclone serum in RPMI was added and left overnight. Fresh medium was added the next day. On the following day polyadenylated RNA was isolated using a MICRO-FASTTRACK mRNA isolation kit (InVitrogen). The RNA was then separated by electrophoresis on a formaldehyde-agarose denaturing gel and then transferred to a nylon membrane (Zetaprobe, Biorad). The membrane was prehybridized in 50% formamide, 5× SSC, 5× Denhardt's solution, 1% SDS and 100 $\mu$g/ml sheared, denatured herring testis DNA for 4 hours at 42° C. The membrane was then hybridized overnight at 42° C. with a 2.0 kb cDNA fragment of MRP labelled with [$\alpha$-$^{32}$P]dCTP using a random prime kit (GIBCO/BRL). The blot was washed three times in 0.1% SDS and 0.1×SSC for 20 minutes at 52° C. and autoradiographed. Only in overloaded lanes was any RNA detectable as a faint band after oligonucleotide treatment with ISIS 7597 and 7598.

Example 6

Diagnostic Assay for MRP-associated Tumors Using Xenografts in Nude Mice

Tumors arising from MRP overexpression are diagnosed and distinguished from other tumors using this assay. A biopsy sample of the tumor is treated, e.g., with collagenase or trypsin or other standard methods, to dissociate the tumor mass. $5 \times 10^6$ tumor cells are implanted in the inner thighs of two or more nude mice. Antisense oligonucleotide suspended in saline is administered to one or more mice by intraperitoneal injection three times weekly beginning on day 4 after tumor cell inoculation. Saline only is given to a control mouse. Oligonucleotide dosage is 25 mg/kg. Tumor size is measured and tumor volume is calculated on the eleventh treatment day. Tumor volume of the oligonucleotide-treated mice is compared to that of the control mouse. The volume of MRP-associated tumors in the treated mice are measurably smaller than tumors in the control mouse. Tumors arising from causes other than MRP overexpression are not expected to respond to the oligonucleotides targeted to the nucleic acids encoding MRP and, therefore, the tumor volumes of oligonucleotide-treated and control mice are equivalent.

Example 7

Detection of MRP Overexpression

Oligonucleotides are radiolabeled after synthesis by $^{32}$P labeling at the 5' end with polynucleotide kinase. Sambrook et al., "*Molecular Cloning. A Laboratory Manual,*" Cold Spring Harbor Laboratory Press, 1989, Volume 2, pg. 11.31–11.32. Radiolabeled oligonucleotide is contacted with tissue or cell samples suspected of MRP overexpression, such as tumor biopsy samples, under conditions in which specific hybridization can occur, and the sample is washed to remove unbound oligonucleotide. A similar control is maintained wherein the radiolabeled oligonucleotide is contacted with normal cell or tissue sample under conditions that allow specific hybridization, and the sample is washed to remove unbound oligonucleotide. Radioactivity remaining in the sample indicates bound oligonucleotide and is quantitated using a scintillation counter or other routine means. Comparison of the radioactivity remaining in the samples from normal and tumor cells indicates overexpression of MRP.

Radiolabeled oligonucleotides of the invention are also useful in autoradiography. Tissue sections are treated with radiolabeled oligonucleotide and washed as described above, then exposed to photographic emulsion according to standard autoradiography procedures. A control with normal cell or tissue sample is also maintained. The emulsion, when developed, yields an image of silver grains over the regions expressing MRP, which is quantitated. The extent of MRP overexpression is determined by comparison of the silver grains observed with normal and tumor cells.

Analogous assays for fluorescent detection of MRP overexpression use oligonucleotides of the invention which are labeled with fluorescein or other fluorescent tags. Labeled DNA oligonucleotides are synthesized on an automated DNA synthesizer (Applied Biosystems model 380B) using standard phosphoramidite chemistry with oxidation by iodine. β-cyanoethyldiisopropyl phosphoramidites are purchased from Applied Biosystems (Foster City, Calif.). Fluorescein-labeled amidites are purchased from Glen Research (Sterling, Va.). Incubation of oligonucleotide and biological sample is carried out as described for radiolabeled oligonucleotides except that instead of a scintillation counter, a fluorescence microscope is used to detect the fluorescence. Comparison of the fluorescence observed in samples from normal and tumor cells indicates MRP overexpression.

---

What is claimed is:

1. A method of decreasing the synthesis of multidrug resistance-associated protein in an animal suspected of having a condition which is characterized by changes in levels of multidrug resistance-associated protein comprising administering to an animal suspected of having a condition which is characterized by changes in levels of multidrug resistance-associated protein an effective amount of an oligonucleotide having 8 to 30 nucleotides complementary to a nucleic acid encoding multidrug resistance-associated protein and capable of decreasing the expression of multidrug resistance-associated protein so that synthesis of multidrug resistance-associated protein is decreased.

2. The method of claim 1 wherein said oligonucleotide is complementary to a transcription initiation site, translation initiation site, 5'-untranslated sequence, 3' untranslated sequence, coding sequence or an intron/exon junction of an mRNA encoding multidrug resistance-associated protein.

3. The method of claim 1 wherein said oligonucleotide is administered in a pharmaceutical composition comprising the oligonucleotide and a pharmaceutically acceptable carrier.

4. The method of claim 1 wherein the oligonucleotide is administered systemically.

5. The method of claim 1 wherein the oligonucleotide is administered in conjunction with a chemotherapeutic drug treatment for cancer.

6. The method of claim 1 wherein the oligonucleotide comprises SEQ ID NO: 2, 3, 4, 5, 6, 7, 8, 9, 10, 11, 12, 13, 14, 15 or 16.

7. The method of claim 6 wherein the oligonucleotide comprises SEQ ID NO: 8 or SEQ ID NO: 9.

8. The method of claim 1 wherein at least one of the intersugar linkages between nucleotides of the oligonucleotide is a phosphorothioate linkage.

9. The method of claim 1 wherein the condition is a multidrug-resistant cancer.

10. The method of claim 9 wherein the multidrug-resistant cancer is small-cell lung cancer.

11. A method for improving the efficacy of a chemotherapeutic drug treatment of a disease, said method comprising administering in conjunction with a chemotherapeutic drug treatment an oligonucleotide comprising 8 to 30 nucleotides complementary to a nucleic acid encoding multidrug resistance-associated protein and capable of decreasing the expression of multidrug resistance-associated protein.

12. The method of claim 1 wherein the oligonucleotide comprises SEQ ID NO: 2, 3, 4, 5, 6, 7, 8, 9, 10, 11, 12, 13, 14, 15 or 16.

13. The method of claim 12 wherein the oligonucleotide comprises SEQ ID NO: 8 or SEQ ID NO: 9.

14. The method of claim 11 wherein at least one of the intersugar linkages between nucleotides of the oligonucleotide is a phosphorothioate linkage.

15. The method of claim 11 wherein the disease is cancer.

16. The method of claim 15 wherein the disease is small-cell lung cancer.

17. A method for preventing the development of multidrug resistance during a chemotherapeutic drug treatment of a disease, said method comprising administering in conjunction with a chemotherapeutic drug treatment an oligonucleotide comprising 8 to 30 nucleotides complementary to a nucleic acid encoding multidrug resistance-associated protein and capable of decreasing the expression of multidrug resistance-associated protein so that synthesis of multidrug resistance-associated protein is decreased.

18. The method of claim 17 wherein the oligonucleotide comprises SEQ ID NO: 2, 3, 4, 5, 6, 7, 8, 9, 10, 11, 12, 13, 14, 15 or 16.

19. The method of claim 18 wherein the oligonucleotide comprises SEQ ID NO: 8 or SEQ ID NO: 9.

20. The method of claim 17 wherein at least one of the intersugar linkages between nucleotides of the oligonucleotide is a phosphorothioate linkage.

21. The method of claim 17 wherein the disease is cancer.

22. The method of claim 21 wherein the disease is small-cell lung cancer.

23. The method of claim 1 wherein at least one of the nucleotides of the oligonucleotide is modified at the 2' position.

24. The method of claim 23 wherein the nucleotide modification is 2'-O-methyl, 2'-O-propyl or 2'-fluoro.

25. The method of claim 11 wherein at least one of the nucleotides of the oligonucleotide is modified at the 2' position.

26. The method of claim 25 wherein the nucleotide modification is 2'-O-methyl, 2'-O-propyl or 2'-fluoro.

27. The method of claim 17 wherein at least one of the nucleotides of the oligonucleotide is modified at the 2' position.

28. The method of claim 27 wherein the nucleotide modification is 2'-O-methyl, 2'-O-propyl or 2'-fluoro.

\* \* \* \* \*

UNITED STATES PATENT AND TRADEMARK OFFICE
CERTIFICATE OF CORRECTION

PATENT NO. : 5,807,838
DATED : September 15, 1998
INVENTOR(S) : Baracchini, et al.

It is certified that error appears in the above-indentified patent and that said Letters Patent is hereby corrected as shown below:

At col 1, line 14, please delete "MRNA" and insert therefor --mRNA--.

At col 2, line 24, please delete "MRNA" and insert therefor --mRNA--.

At col 3, line 29, please delete "MRNA" and insert therefor --mRNA--.

In claim 12, line 1, delete "claim 1" and insert therefor --claim 11--.

Signed and Sealed this

Second Day of February, 1999

Attest:

*Acting Commissioner of Patents and Trademarks*

*Attesting Officer*